United States Patent
Kazuhiro et al.

(10) Patent No.: US 6,280,378 B1
(45) Date of Patent: Aug. 28, 2001

(54) FLUORESCENCE ENDOSCOPE

(75) Inventors: Tsujita Kazuhiro; Tomonari Sendai, both of Kanagawa-ken (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/322,159

(22) Filed: May 28, 1999

(30) Foreign Application Priority Data

May 29, 1998 (JP) .................................................. 10-148666

(51) Int. Cl.[7] ........................................................ A61B 1/04
(52) U.S. Cl. ............................ 600/160; 600/109; 348/65; 348/68
(58) Field of Search ..................................... 600/109, 160; 348/65, 68, 70, 71, 222

(56) References Cited

U.S. PATENT DOCUMENTS

| | | | |
|---|---|---|---|
| 4,902,115 | 2/1990 | Takahashi | 350/449 |
| 4,961,110 | * 10/1990 | Nakamura | 348/70 |
| 5,879,284 | 3/1999 | Tsujita | 600/109 |

* cited by examiner

Primary Examiner—John Mulcahy
(74) Attorney, Agent, or Firm—Sughrue, Mion, Zinn, Macpeak & Seas, PLLC

(57) ABSTRACT

A fluorescence endoscope includes an illuminating light projecting system which projects illuminating light onto a part inside a body, a first objective optical system which causes the illuminating light reflected at the part of the body to form a normal image of the part, an excitation light projecting system which projects onto a part inside the body excitation light, and a second objective optical system which causes fluorescence emitted from the part to form a fluorescence image. A normal image CCD takes the image formed by the objective optical system and outputs a normal image signal representing the normal image and a fluorescence image CCD takes the fluorescence image formed by the second objective optical system and outputs a fluorescence image signal representing the fluorescence image. A measuring light projecting system projects measuring light at a wavelength in the wavelength range of the fluorescence onto a part inside the body. Measurement images are formed through the first and second objective optical systems by the measuring light reflected at the same part of the body and an image degradation function of the second objective optical system is obtained on the basis of the image signals. An image restoration processing is carried out on a fluorescence image signal on the basis of the image degradation function.

5 Claims, 1 Drawing Sheet

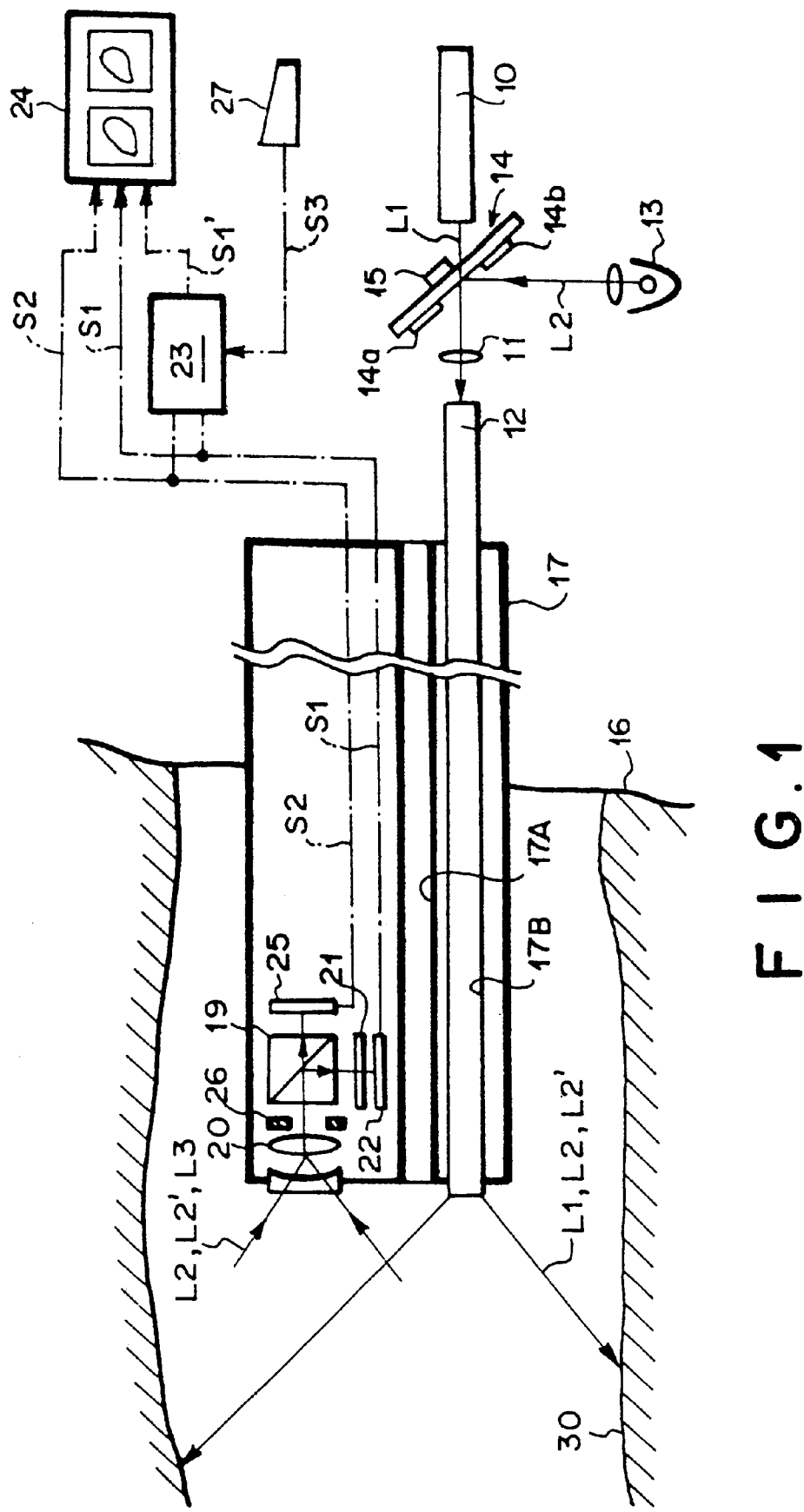
F I G. 1

FLUORESCENCE ENDOSCOPE

BACKGROUND OF THE INVENTION

1. Field of the Invention

This invention relates to a fluorescence endoscope used to examine the interior of a body cavity and the like, and more particularly to a fluorescence endoscope in which blur of the image due to insufficient depth of focus of the objective optical system can be avoided.

2. Description of the Related Art

There has been in wide use an endoscope to observe the interior of a body cavity or to give treatment observing the interior of a body cavity. Currently an electronic endoscope comprising an illuminating light projecting system which projects illuminating light onto a part inside a body through optical fibers or like, an objective optical system which is inserted into the interior of the body and forms an image of the part by the light reflected at the part of the body and an image taking means which takes the image formed by the objective optical system is major.

On the other hand, there have been made various investigations on photodynamic diagnosis (PDD). The photodynamic diagnosis is a technique in which a photosensitive material which has affinity to tumor and emits fluorescence when excited by light is first administered to the tumor, excitation light having a wavelength in the excitation wavelength range of the photosensitive material is projected onto the tissue, and then the intensity of the fluorescence is measured or the tumor is diagnosed on the basis of an image formed by the fluorescence. As another form of the photodynamic diagnosis, there has been known a technique in which excitation light having a wavelength in the exciting range of a photosensitive material inherent to the organism is projected onto the organism to cause the intrinsic photosensitive material to emit fluorescence (so-called auto-fluorescence), and tumor is diagnosed on the basis of an auto-fluorescence image.

A fluorescence endoscope for taking such a fluorescence image and displaying the image basically comprises an excitation light projecting system which projects excitation light onto a part inside the body in addition to said illuminating light projecting system, the objective optical system and the image taking means, and an image formed by fluorescence emitted from the part is taken by the image taking means.

In such a fluorescence endoscope, use of an objective optical system which is small in F-number and high in numerical aperture is generally required in order to efficiently detect fluorescence which is normally very weak. However when a high numerical aperture objective optical system is used, the depth of focus is reduced and blur is apt to be generated in a part of the fluorescence image taken.

As an objective optical system for an endoscope in which the depth of focus can be increased, there has been known one disclosed, for instance, in Japanese Patent Publication No. 7(1995)-119893. The objective optical system is provided with an adjustable diaphragm and when a part relatively close to the optical system is to be observed, the diaphragm is closed to increase the depth of focus.

However since fluorescence emitted from a part inside the body is very weak as described above, the method of increasing the depth of focus by closing the diaphragm is difficult to apply to the fluorescence endoscope.

In order to overcome the aforesaid problem, we have proposed to carry out, in an endoscope comprising an objective optical system which is inserted into the interior of an organic body and an image taking means which takes an image formed by the objective optical system and outputs an image signal representing the image, an image restoration processing on a part of the image signal corresponding to a predetermined range in the image taking range of the image taking means by use of a degradation function such as a point spread function of the objective optical system. See Japanese Unexamined Patent Publication No. 10(1998)-165365.

In the endoscope, blur of an image due to insufficient depth of focus of the objective optical system can be removed by an image restoration processing using a degradation function such as a point spread function or the like of the objective optical system. When blur of the image due to insufficient depth of focus of the objective optical system can be avoided in this manner, a high numerical aperture objective optical system can be employed and accordingly the amount of light entering the image taking means can be increased.

However in the endoscope, since a preset design value or a measured value is employed as the degradation function, it is difficult to accurately restore the image taking into account change of the degradation function which is caused, for instance, when the position of the endoscope relative to the part to be observed changes.

The problem may be overcome, when the endoscope is arranged to measure the distance between each point on the part to be observed and the endoscope and to carry out the image restoration processing on a part of the image signal corresponding to the part of the body whose distance from the endoscope is within a predetermined range. However this approach is disadvantageous in that it requires a distance measuring means, which complicates the structure of the endoscope.

SUMMARY OF THE INVENTION

In view of the foregoing observations and description, the primary object of the present invention is to provide an endoscope in which the image restoration processing can be accurately carried out even if the position of the endoscope relative to the part to be observed changes without use of a distance measuring means.

In accordance with the present invention, there is provided a fluorescence endoscope comprising an illuminating light projecting system which projects illuminating light onto a part inside a body, a first objective optical system which is inserted into the interior of the body and causes the illuminating light reflected at the part of the body to form a normal image of the part, a normal image taking means which takes the image formed by the objective optical system and outputs a normal image signal representing the normal image, an excitation light projecting system which projects onto a part inside the body excitation light having a wavelength in the excitation wavelength range of a photosensitive material, a second objective optical system which causes fluorescence emitted from the part to form a fluorescence image, and a fluorescence image taking means which takes the fluorescence image formed by the second objective optical system and outputs a fluorescence image signal representing the fluorescence image, wherein the improvement comprises a measuring light projecting system which projects measuring light having a wavelength in the wavelength range of the fluorescence onto a part inside the body, an operation means which obtains an image degradation function of the second objective optical system through operation using image signals respectively output from the normal image taking means and the fluorescence image taking means on the basis of images formed through the first and second objective optical systems by the measuring light reflected at the same part of the body, and an image processing means which carries out an image restoration processing on a fluorescence image signal output from the fluorescence image taking means on the basis of the image degradation function.

As the measuring light projecting system, those which emit light substantially equal in spectrum to the fluorescence emitted from the part of the body upon exposure to the excitation light or light having a wavelength substantially equal to a main peak wavelength of the fluorescence can be suitably employed.

As the degradation function, a point spread function of the second objective optical system can be suitably used.

The first and second objective optical systems may be formed either separately from each other or as a single objective optical system common to the normal image taking means and the fluorescence image taking means.

However when the first and second objective optical systems are formed separately from each other, parallax between the objective optical systems can cause distortion of the image. Accordingly, in such a case, it is preferred that the endoscope be further provided with a means for carrying out processing for correcting distortion of the image due to parallax between the first and second objective optical systems on the image signals respectively output from the normal image taking means and the fluorescence image taking means.

In the fluorescence endoscope in accordance with the present invention, images formed through the first and second objective optical systems by the measuring light reflected at the same part of the body are taken by the normal image taking means and the fluorescence image taking means, and an image degradation function of the second objective optical system is obtained by performing operation on the basis of the image signals output from the normal image taking means and the fluorescence image taking means. Since the degradation function thus obtained is based on data on images which are actually taken, the degradation function precisely reflects the actual position of the endoscope relative to the part to be observed. Accordingly provided that the position of the endoscope relative to the part to be observed when taking a fluorescence image is held unchanged from that when the degradation function is obtained, an extremely accurate image restoration processing can be carried out using a degradation function which precisely reflects the actual position of the endoscope relative to the part to be observed, whereby blur of an image due to insufficient depth of focus of the objective optical system can be well removed.

Further in the fluorescence endoscope of the present invention, since there is required no distance measuring means, the structure of the endoscope can be relatively simple.

It has been known that blur of an image can be effectively removed by an image restoration processing using a point spread function or the like of the objective optical system as a degradation function. Degradation functions of images can be roughly divided into those which represent degradation by a point spread function which can be analytically determined and those which represent degradation by a point spread function which cannot be analytically determined. In the present invention, the degradation by the point spread function can be known by actually measuring the input and output of the objective optical system and accordingly a degradation function in the former group can be suitably used. In this case, the image can be restored by de-convolution.

When the image is restored by the deconvolution, a filtering processing is generally applied. At this time, when noise can be ignored, the image can be restored by applying a so-called reverse filter to Fourier transform of the degraded image.

On the other hand, when noise cannot be ignored, the image can be restored by use of a least square filter (wiener filter) which minimizes the mean square error between the original image and the restored image, a limited reverse convolution filter, a recursive filter, a homomorphism filter, or the like.

Such an image restoration processing is described in detail, for instance, in papers of "Academy of Electronic Communication", November, 1984, Vol. J67-D, No.10, and "O plus E" magazine", an extra number, November, 1986. All the image restoration processings described there can be used in the present invention.

BRIEF DESCRIPTION OF THE DRAWING

FIG. 1 is a schematic side view of a fluorescence endoscope in accordance with an embodiment of the present invention.

DESCRIPTION OF THE PREFERRED EMBODIMENT

In FIG. 1, a fluorescence endoscope in accordance with an embodiment of the present invention comprises an excitation light source 10 such as a SHG laser which generates excitation light L1, for instance, in a blue region, a condenser lens 11 which condenses the excitation light L1 and a light guide 12 which is formed of optical fibers and is disposed so that the condensed excitation light L1 enters the light guide 12. The endoscope is further provided with an illuminating light source 13 which emits white illuminating light L2 in a direction perpendicular to the optical path of the excitation light L1, a filter wheel 14 which is disposed on the optical path of the excitation light L1 at 45° thereto, and a drive means 15 which rotates the filter wheel 14.

The filter wheel 14 is provided with a mirror 14a and a dichroic mirror 14b fixed thereto. The mirror 14a reflects the illuminating light as it is toward the condenser lens 11. The dichroic mirror 14b reflects only a component of the illuminating light L2, which is white light, having a wavelength substantially equal to a peak wavelength of fluorescence L3 to be described later toward the condenser lens 11 as measuring light L2'. Further the filter wheel 14 is provided with an opening through which the excitation light L1 passes the filter wheel 14 to impinge upon the condenser lens 11.

The filter wheel 14 is driven by the drive means 15 and is selectively positioned in one of a first position where the opening is on the optical path of the excitation light L1 so that the excitation light L1 passes the filter wheel 14 and impinges upon the condenser lens 11, a second position where the mirror 14a reflects the illuminating light L2 toward the condenser lens 11 and a third position where the dichroic mirror 14b reflects the measuring light L2' toward the condenser lens 11.

The light guide 12 is contained in a forceps passage 17B in a flexible probe 17 which is inserted into a body 16. A beam splitter 19 is disposed in the probe 17 and an objective lens 20 is disposed forward of the beam splitter 19.

The beam splitter 19 reflects downward a part of light impinging thereon and transmits the other part of the light as will be described later. A excitation light cut filter 21 and a fluorescence image taking means 22 are disposed in this order below the beam splitter 19. The fluorescence image taking means 22 may comprise, for instance, a CCD, and the fluorescence image taking means 22 is connected to an image processing system 23 and an image display system 24 which may comprise, for instance, a CRT. The light passing through the beam splitter 19 impinges upon a normal image taking means 25, which may comprise, for instance, a CCD. The normal image taking means 25 is also connected to the image processing system 23 and the image display system 24.

Operation of the fluorescence endoscope will be described hereinbelow. A photosensitive material which has affinity to tumor and emits fluorescence when excited by light has been absorbed by a diagnostic part 30 of the body 16. The photosensitive material may be, for instance, porphyrin. When the excitation light L1 is projected onto the diagnostic part 30, the photosensitive material emits fluorescence L3 and when the illuminating light L2 or the measuring light L2' is projected onto the diagnostic part 30, the illuminating light L2 or the measuring light L2' is reflected by the diagnostic part 30.

When a normal image is to be observed, the illuminating light source 13 is energized, and the filter wheel 14 is rotated to the second position where the mirror 14a reflects the illuminating light L2 toward the condenser lens 11. The illuminating light L2 emitted from the illuminating light source 13 is condensed by the condenser lens 11 and enters the light guide 12. The illuminating light L2 propagates through the light guide 12 and emanates from the front end of the light guide 12 to illuminate the diagnostic part 30.

A part of the illuminating light L2 reflected by the diagnostic part 30 passes through the beam splitter 19 to impinge upon the normal image taking means 25. At this time, a normal image of the diagnostic part 30 by the reflected illuminating light L2 is formed on the normal image taking means 25 by the objective lens 20, and the normal image is taken by the normal image taking means 25. An image signal S2, representing the normal image, output from the normal image taking means 25 is input into the image display means 24 and the normal image is displayed by the image display means 24.

An adjustable diaphragm 26 is disposed between the objective lens 20 and the beam splitter 19 and is closed to a predetermined diameter to increase the depth of focus of the objective lens 20 when the normal image is taken.

When a fluorescence image is to be taken, the excitation light source 10 is energized and the filter wheel 14 is rotated to the first position where the opening is on the optical path of the excitation light L1 so that the excitation light L1 passes the filter wheel 14 and impinges upon the condenser lens 11. The excitation light L1 emitted from the excitation light source 10 is condensed by the condenser lens 11 and enters the light guide 12. The excitation light L1 propagates through the light guide 12 and emanates from the front end of the light guide 12 to impinge upon the diagnostic part 30.

When the excitation light L1 is projected onto the diagnostic part 30, the photosensitive material which has been absorbed by the diagnostic part 30 emits fluorescence L3. A part of the fluorescence L3 is reflected by the beam splitter 19 to impinge upon the fluorescence image taking means 22. At this time a fluorescence image of the diagnostic part 30 by the fluorescence L3 is formed on the fluorescence image taking means 22 by the objective lens 20 and the fluorescence image is taken by the fluorescence image taking means 22. The excitation light L1 which is reflected by the diagnostic part 30 and travels toward the fluorescence image taking means 22 is cut by the excitation light cut filter 21.

An image signal S1, representing the fluorescence image, output from the fluorescence image taking means 22 is input into the image display means 24 and the fluorescence image is displayed by the image display means 24. Since the photosensitive material has affinity to tumor, only an image of the tumor part is basically displayed.

When the fluorescence image is taken, the adjustable diaphragm 26 is full opened so that the weak fluorescence L3 enters the fluorescence image taking means 22 as much as possible. When the adjustable diaphragm 26 is full opened, the depth of focus of the objective lens 20 is reduced and blur is apt to be generated in a part of the fluorescence image taken. Removal of such blur will be described hereinbelow.

The fluorescence image signal S1 output from the fluorescence image taking means 22 is also input into the image processing system 23 and is subjected to an image restoration processing using a point spread function of the objective lens 20. Specifically a deconvolution processing using the aforesaid various filters is carried out as the image restoration processing.

Out of such processings, a typical processing using a so-called reverse filter will be described below.

When a coordinate system for the whole image is expressed by (x, y) and a coordinate system for a part of the image is expressed by (x', y') while the original image and the degraded image are expressed respectively by f(x, y) and g(x, y), the following relation holds.

$$g(x,y)=\int\int h(x,y,x',y')f(x',y')dx'dy'+n(x,y)$$

wherein, h(x, y, x', y') is a degradation function, and n(x,y) is noise. When there is no noise, a degraded image of a point light source represented by f(x', y')=δ(x'−α), y'−β) is h(x, y, α, β). Accordingly h(x, y, α, β) is a point spread function which is independent of the position (α, β) of a point on the original image.

If a degraded image of a point does not exists in the position of the point except translation, the above relation is expressed by convolution as follows.

$$g(x,y)=\int\int h(x-x',y-y')f(x', y')dx'dy'+n(x,y)$$

When it is assumed that noise is negligible, the above formula may be as follows.

$$g(x,y)=\int\int h(x-x',y-y')f(x',y')dx'dy'$$

When taking Fourier transforms of the both sides of this formula and convolution theorem is applied thereto, the following formula holds.

$$G(u,v)=H(u,v)F(u,v)$$

wherein F(u, v), G(u, v) and H(u, v) are Fourier transforms of f(x, y), g(x, y) and h(x, y), respectively, and H(u, v) is a transfer function of a system for converting an original image f(x, y) to a degraded image g(x, y).

By taking a reverse Fourier transform of G(u, v)/H(u, v), the original image can be restored. Accordingly 1/H(u, v) is referred to as "a reverse filter".

The image signal S1' which has been subjected to the image restoration processing is input into the image display means 24 and a fluorescence image is displayed by the image display means 24 on the basis of the image signal S1'. In this particular embodiment, the fluorescence image is displayed on the image display means 24 together with a fluorescence image reproduced on the basis of the original image signal S1. This arrangement allows the restored image to be compared with the original image, whereby the effect of the image restoration processing can be confirmed.

Further in the embodiment described above, the command for carrying out the image restoration processing on the image signal S1 is manually input by use of an input means 27 such as a keyboard. Accordingly, whether the image restoration processing is to be carried out can be selected.

However since blur is apt to be generated when the adjustable diaphragm 26 is in full open, it is possible to input the control signal of the adjustable diaphragm 26 also into the image processing system 23 and to automatically carry out the image restoration processing when the diaphragm 26 is full opened. This simplifies the operation of the operator.

Determination of the point spread function of the objective lens 20, i.e., the degradation function h(x, y, x', y'), will be described hereinbelow. When determining the point spread function, the illuminating light source 13 is energized and the filter wheel 14 is rotated to the third position where the dichroic mirror 14b reflects the measuring light L2' toward the condenser lens 11. The component of the illuminating light L2 having a wavelength substantially equal to a peak wavelength of fluorescence L3 is reflected by the dichroic mirror 14b toward the condenser lens 11 as measuring light L2'. The measuring light L2' is condensed by the condenser lens 11 and enters the light guide 12. The measuring light L2' propagates through the light guide 12 and emanates from the front end of the light guide 12 to impinge upon the diagnostic part 30.

A part of the measuring light L2' reflected by the diagnostic part 30 passes through the beam splitter 19 and impinges upon the normal image taking means 25. At this time, an image (measurement image) of the diagnostic part 30 by the measuring light L2' is formed on the normal image taking means 25 by the objective lens 20, and the measurement image is taken by the normal image taking means 25. An image signal S2, representing the measurement image, output from the normal image taking means 25 is input into the image processing system 23.

When the measurement image is taken, the adjustable diaphragm 26 is kept closed.

Thereafter, the adjustable diaphragm 26 is full opened and an measurement image is taken by the fluorescence image taking means 22. Also, in this case, the measuring light L2' is projected onto the diagnostic part 30 and a part of the measuring light L2' reflected by the diagnostic part 30 is reflected by the beam splitter 19 to impinge upon the fluorescence image taking means 22. At this time, a measurement image of the diagnostic part 30 by the measuring light L2' is formed on the fluorescence image taking means 22 by the objective lens 20, and the measurement image is taken by the fluorescence image taking means 22. An image signal S1, representing the measurement image, output from the fluorescence image taking means 22 is input into the image processing system 23.

In this example, since the images taken by the normal image taking means 25 and the fluorescence image taking means 22 are formed by the same objective lens 20, the image signals S2 and S1 represent images of the same part.

The image processing system 23 calculates a deterioration function h(x, y, x', y') for each position (x, y) on the basis of the image signals S1 and S2 thus input into the image processing system 23. The image processing system 23 stores the deterioration functions h(x, y, x', y') thus obtained in a built-in memory and reads out the same when the aforesaid image restoration processing is to be carried out.

The processing of obtaining the deterioration functions h(x, y, x', y') is carried out just before a fluorescence image is taken and displayed. When the fluorescence image is taken and displayed, the position of the objective lens 20 relative to the diagnostic part is held unchanged from that when the degradation functions are obtained. In this manner, an extremely accurate image restoration processing can be carried out using the degradation functions h(x, y, x', y') which precisely reflect the actual position of the objective lens 20 relative to the diagnostic part 30.

In general clinical treatment and the like, a step of displaying a normal image of a tumor suspect portion and observing the same, a step of taking the measurement images with the adjustable diaphragm full opened and obtaining the degradation functions, and a step of taking a fluorescence image and restoring the fluorescence image are performed in sequence.

When a fluorescence image is taken and displayed, unevenness on the diagnostic part 30 makes ununiform the amount of the excitation light L1 to which each portion of the diagnostic part is exposed, which results in fluctuation in the intensity of the fluorescence L3. The fluctuation in the intensity of the fluorescence L3 due to ununiformity of the excitation light L1 cannot be distinguished from that due to fluctuation in the concentration of the photosensitive material, that is, fluctuation in the intensity of the fluorescence L3 depending on the condition of the tumor.

In such a case, by taking a measurement image of the diagnostic part 30 by the measuring light L2, just before taking a fluorescence image and normalizing a fluorescence image signal S1' on the basis of the image signal representing the measurement image, the components due to ununiformity of the excitation light L1 can be removed.

In the embodiment described above, a single objective lens 20 is used both for forming the normal image and the fluorescence image, and the normal image and the fluorescence image are taken by separate image taking means 25 and 22.

However the normal image and the fluorescence image may be formed by separate objective optical systems. In this case, parallax between the objective optical systems can cause distortion of the image. Accordingly, in such a case, it is preferred that the image signals S1 and S2 output from the fluorescence image taking means 22 and the normal image taking means 25 when the measurement images are taken be subjected to processing for correcting distortion of the images due to parallax between the objective optical systems. For example, the correction can be performed by coordinate transformation using correction data depending on distortion of the images due to parallax which are stored in a look-up table.

Further in the fluorescence endoscope of the present invention, both an objective optical system and an image taking means may be used for taking a normal image and taking a fluorescence image. However, even in this case, it is impossible for the single image taking means to take measurement images through the normal image taking system and the fluorescence image taking system at one time.

Accordingly, it is necessary to take a measurement image through the normal image taking system with the adjustable diaphragm closed and then take a measurement image through the fluorescence image taking system with the adjustable diaphragm full opened.

Though, in the embodiment described above, a photosensitive material is given to the diagnostic part in advance, the present invention may be applied to a case where a fluorescence image formed by auto-fluorescence emitted from the intrinsic photosensitive material is taken.

What is claimed is:

1. A fluorescence endoscope comprising an illuminating light projecting system which projects illuminating light onto a part inside a body, a first objective optical system which is inserted into the interior of the body and causes the illuminating light reflected at the part of the body to form a normal image of the part, a normal image taking means which takes the image formed by the objective optical system and outputs a normal image signal representing the normal image, an excitation light projecting system which projects onto a part inside the body excitation light having a wavelength in the excitation wavelength range of a photosensitive material, a second objective optical system which causes fluorescence emitted from the part to form a fluorescence image, and a fluorescence image taking means which takes the fluorescence image formed by the second objective optical system and outputs a fluorescence image signal representing the fluorescence image, wherein the improvement comprises a measuring light projecting system which projects measuring light having a wavelength in the wavelength range of the fluorescence onto a part inside the body, an operation means which obtains an image degradation function of the second objective optical system through operation using image signals respectively output from the normal image taking means and the fluorescence image taking means on the basis of images formed through the first and second objective optical systems by the measuring light reflected at the same part of the body, and an image processing means which carries out an image restoration processing on a fluorescence image signal output from the fluorescence image taking means on the basis of the image degradation function.

2. A fluorescence endoscope as defined in claim 1 in which the measuring light projecting system emits light substantially equal in spectrum to the fluorescence emitted from the part of the body upon exposure to the excitation light.

3. A fluorescence endoscope as defined in claim 1 in which the measuring light projecting system emits light having a wavelength substantially equal to a main peak wavelength of the fluorescence emitted from the part of the body upon exposure to the excitation light.

4. A fluorescence endoscope as defined in claim 1 in which the degradation function is a point spread function of the second objective optical system.

5. A fluorescence endoscope as defined in claim 1 in which the first and second objective optical systems are formed separately from each other and there is provided a means for carrying out processing for correcting distortion of the image due to parallax between the first and second objective optical systems on the image signals respectively output from the normal image taking means and the fluorescence image taking means.

* * * * *